US008507254B1

(12) United States Patent
Abuhasel

(10) Patent No.: US 8,507,254 B1
(45) Date of Patent: Aug. 13, 2013

(54) PROCESS OF GROWING AND HARVESTING ALGAE IN SEAWATER WITH FEATHER ADDITIVE

(76) Inventor: Khaled Ali Abuhasel, Las Cruces, NM (US)

( * ) Notice: Subject to any disclaimer, the term of this patent is extended or adjusted under 35 U.S.C. 154(b) by 0 days.

(21) Appl. No.: 13/542,395

(22) Filed: Jul. 5, 2012

(51) Int. Cl.
C12N 1/12 (2006.01)

(52) U.S. Cl.
USPC ........... 435/257.1; 435/267; 435/134; 47/1.4; 800/296; 71/15

(58) Field of Classification Search
None
See application file for complete search history.

(56) References Cited

U.S. PATENT DOCUMENTS

| 2009/0324799 | A1* | 12/2009 | Hartman et al. ............ 426/635 |
| 2010/0267122 | A1* | 10/2010 | Chinnasamy et al. ..... 435/257.3 |
| 2010/0297749 | A1 | 11/2010 | Aravanis et al. |
| 2011/0143012 | A1 | 6/2011 | Rettenmaier |
| 2011/0201063 | A1 | 8/2011 | Mitropoulos |

OTHER PUBLICATIONS

Briassoulis D et al. An experimental helical-tubular photobioreactor for continuous production of *Nannochloropsis* sp. 101: 6768-6777, 2010.*
Boushy AR et al. Feather meal—a biological waste: its processing and utilization as a feedstuff for poutry. 32: 39-74, 1990.*
Subhadra BG. Sustainability of algal biofuel production using intergrated renewable energy park (IREP) and algal biorefinery approach. 38: 5892-5901, 2010.*
Day JG et al. In vitro culture and conservation of microalgae: applications for aquaculture, biotechnology and environmental research. 35: 127-136, 1999.*
Noval JJ et al, Decomposition of Native Keratin by Streptomyces Fradiae, J Bacteriol 77: 251-263, 1959.*
"Brines (reject concentrate) from desalination", AlgaeArt Technologies Ltd., Shfeyah Agricultural School, MP Hof Carmel 30806, Israel, pp. 1-5, 2012.
"Phycoremediation of Landfill Permeate: A Mini Life Cycle Analysis", Sinclair Vincent—BioEnergy Summer School, Bioenergy and Sustainable Technology Laboratory, 18 pages, (2011).
"National Algal Biofuels Technology Roadmap", John Ferrell and Valerie Sarisky-Reed, U.S. Department of Energy, Energy Efficiency & Renewable Energy, Biomass Program, May 2010, 138 pages.

* cited by examiner

*Primary Examiner* — Jon P Weber
*Assistant Examiner* — Chunyuan Luo
(74) *Attorney, Agent, or Firm* — Oblon, Spivak, McClelland, Maier & Neustadt, L.L.P.

(57) ABSTRACT

A process for mixing seawater, feather additive, and one or more algae to prepare a nutrient-rich feedstock for cultivating, growing, and harvesting algae. The harvested algae are processed to produce biofuel, oil, nutrient supplements, and polymers used for cosmetics.

11 Claims, 3 Drawing Sheets

PROCESS OF GROWING AND HARVESTING ALGAE IN SEAWATER WITH FEATHER ADDITIVE

GRANT OF NON-EXCLUSIVE RIGHT

This application was prepared with financial support from the Saudi Arabian Cultural Mission (SACM), and in consideration therefore the present inventor has granted The Kingdom of Saudi Arabia a non-exclusive right to practice the present disclosure.

BACKGROUND

1. Field of the Disclosure

The present application relates to growing and harvesting algae in seawater, and more particularly, relates to growing and harvesting algae in a mixture of seawater and feather additives.

2. Description of Related Art

Seawater presents plentiful and viable resource for growing and harvesting microalgae for commercial production. Using seawater as a nutrient source for microalgae offers many advantageous possibilities. It provides an inexpensive resource to grow microalgae and it is highly accessible. Purification of seawater for human consumption is difficult and costly. Growing microalgae in seawater reduces a salinity of the seawater and as a result, the purification of seawater with reduced salinity is easier. The reduced salinity of seawater after growing microalgae is due to the fact that microalgae naturally purify the aqueous saline solution in which they inhabit. Microalgal production facilities built along coastlines or farther out to sea may serve to facilitate large-scale microalgae production for commercial purposes. Alternatively, it is possible to modify a large cargo ship such as an oil tanker to serve as a microalgae production facility. The ship may intake seawater to constantly supply the microalgae with necessary nutrients. It may be possible to design a type of mobile microalgal production facility which can ship the microalgae byproducts to commercial ports for further processing. For example, a fleet of tanker ships may be designed that not only transport biofuel, but also their engines are running off of the biofuel and they are perpetually producing the biofuel. This application aims to optimize a microalgal biomass production output. Feather additive mixed with seawater and a specific strain of microalgae optimizes biomass output under controlled conditions.

BRIEF SUMMARY

The present disclosure aims to provide a process for effectively using seawater to grow and harvest algae. In the present application, the process includes growing and harvesting algae in a mixture of seawater and feather additive. Such a mixture provides a nutrient-rich feedstock for growing and harvesting algae. The harvested algae may be used in various applications including, but not limited to, biofuel, oil production, nutrient supplements, and cosmetics.

It is an object of the invention to provide a method for utilizing seawater to produce valuable algal by-products.

It is an object of the invention to provide a Method for growing algae in seawater.

It is an object of the invention to provide a method for growing and harvesting algae utilizing seawater and feather fiber as a growth medium.

It is an object of the invention to provide a method for recycling seawater and feather waste into valuable by-products.

It is an object of the invention to produce a growth solution by mixing feather fiber as a nutrient source with seawater and at least one strain of microalgae in order for that strain to reproduce.

It is an object of the invention to harvest the algae from the product solution to produce a harvested algae product.

It is an object of the invention to separate the harvested algae product from the product solution to produce a concentrated biomass and a remaining solution.

It is an object of the invention to process the concentrated biomass to produce biofuel.

It is an object of the invention to grow plants or microorganisms, for example, halophytes or brine shrimps, in the remaining solution.

It is an object of the invention to desalinate remaining seawater from microalgae production process in order to further purify the seawater source for human or animal consumption.

It is an object of the invention to use feather additive for growing algae in the form of, for example, unprocessed feather, washed feather, clump of feather, feather extract, compact feather, chemically modified feather, or feather powder.

It is an object of the invention to use chicken feather, turkey feather, and/or ostrich feather for growing algae.

It is an object of the invention to use microalgae in the *Nannochloropsis* genus, for example, *Nannochloropsis gaditana, Nannochloropsis granulate, Nannochloropsis limnetica, Nannochloropsis oceanica*, and/or *Nannochloropsis salina* for growing algae in a solution of seawater and feather additive.

It is an object of the invention to process the remaining solution to produce recycled seawater and recycled feather additive in order to re-use it for producing additional products.

It is an object of the invention to use the recycled seawater and the recycled feather additive to reproduce, grow, and harvest algae.

It is an object of the invention to process the concentrated biomass to produce an omega 3 nutrient source for human and animal consumption, fertilizer, vitamins, oil, biofuel, cosmetics, and other products.

It is an object of the invention to adjust light, carbon dioxide, nutrient, salinity, feather content, and nitrogen content for a duration of time in order to effectively grow a quantity of microalgae.

It is an object of the invention to grow algae in two or more phases that include a phase of "feather enrichment" in which nutrients for microalgae are made available and/or a phase where no "feather enrichment" takes place to increase lipid productivity in the microalgae cells.

It is an object of the invention to grow algae in feather extracts, for example, keratin.

DETAILED DESCRIPTION

Figure 1:
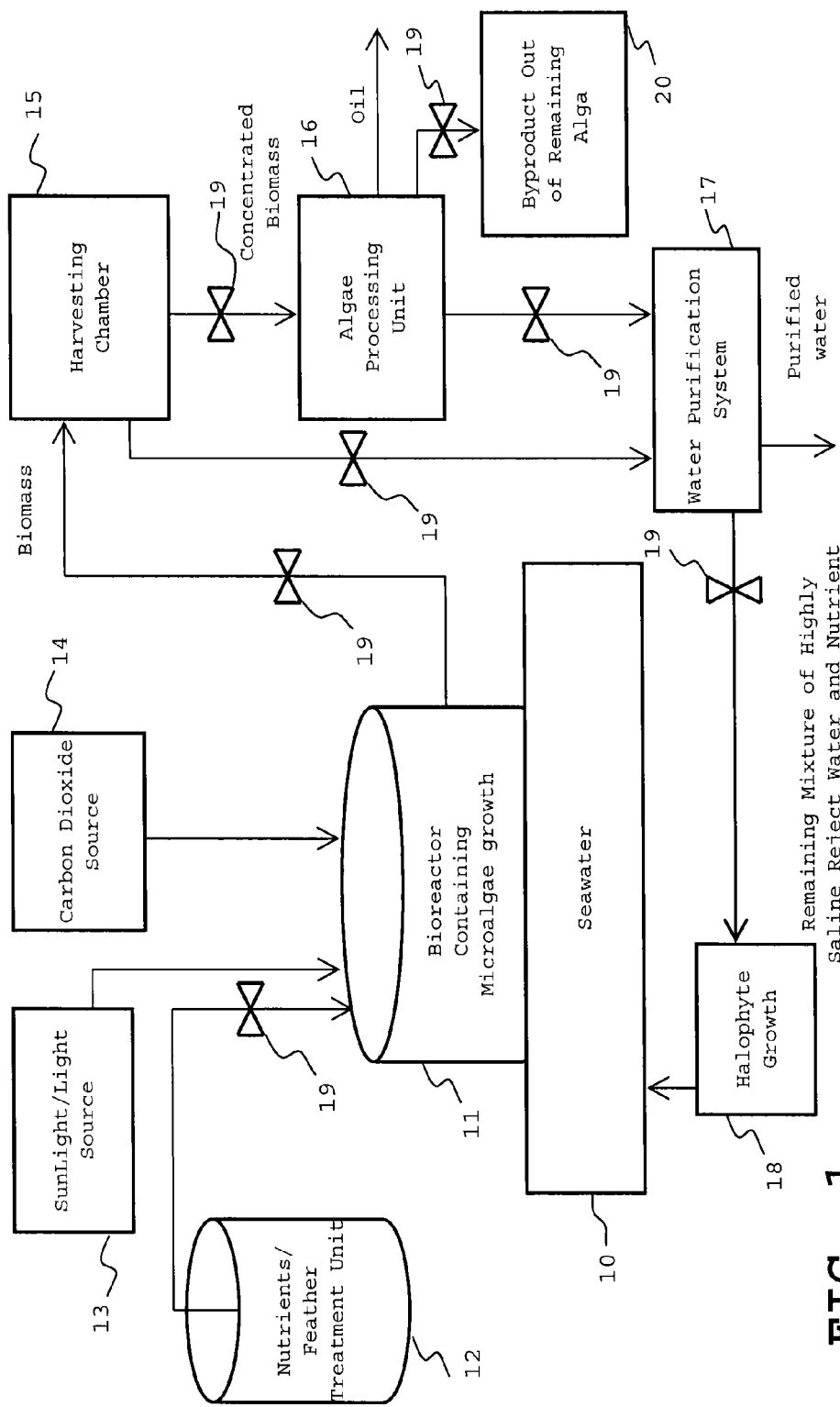
FIG. 1 is a process flow diagram for using seawater for harvesting algae.

An exemplary process flow diagram illustrating the use of seawater for growing and harvesting algae is displayed in FIG. 1. The growing and harvesting algae may occur in a production facility, such as a modified oil tanker or shoreline facility. First, the seawater 10 serves as a platform or space on which an open-pond bioreactor 11 is situated containing the microalgae strain and growth solution. A filter may also be situated inside the bioreactor to prevent excess feather residue from accumulating in the growth solution which may hinder biomass extraction. Seawater may be delivered into the bioreactor 11 at controlled levels during specific intervals in the microalgae production process. A nutrient/feather treatment unit 12 may house grinder mechanisms which mechanically decreases the surface area of the feather additive allowing it to be more effectively absorbed into the growth solution and to be utilized by the microalgae when added. A control valve 19 controls addition of nutrient/feather. A light source 13, for example, sunlight, serves as a light source for the effective growth of microalgae. Fluorescent lamps, tungsten lamps, or other light sources may also be used. A carbon dioxide source 14 is used to provide carbon dioxide, preferably from industrial exhausts that produce high amounts of carbon dioxide. This may help to reduce the adverse environmental effects or the green house effect of carbon dioxide. The resulting biomass is then sent to a harvesting chamber 15 which incorporates a centrifuge to separate the water from the biomass. Similar methods of algae separation may be used. Then, some of the algal biomass is recycled back into the bioreactor 11 and used to reproduce the microalgae. Then, the biomass is delivered to an algae processing unit 16 where the biomass is heated by, for example, a UV lamp, an oven, or other heating mechanism/sources that dehydrate the biomass. A mechanical press extracts oil from the dried algal biomass. Then, the remaining dry biomass product is sent to a holding container 20 where it remains to be used for producing other by-products, for example, vitamin supplements, cosmetics, etc. The wastewater is sent to a water purification system 17 for further desalinization. The highly saline reject water may be used in a halophyte growth area 18 before being delivered to seawater.

The pH value of the seawater is preferably 5 to 8, or more preferably 6 to 7. Alternately, the preferred ranges of pH are, 2 to 5, 3 to 4, 8 to 11, or 9 to 10. The feather fiber additive may be used to control the pH level around 7-8. It should be noted that the functionality of the method described in this application is independent of the source from which seawater is provided.

Salinity may be described as total dissolved solids (TDS) in ppm, for example, 10-50,000 ppm. The salinity is preferably 50-10,000 ppm, 100-5,000 ppm, 200-2,000 ppm, 300-1,000 ppm, or 400-800 ppm.

When the feather nutrient source is added to the seawater, the majority of undissolved solid material is composed of the feather additive which is preferably, around 50%, 60%, 70%, 80%, 90%, or 95%. The feather nutrient source may include one type of feather or different types of feather. The feather may be processed before being added to the seawater. For example, the feather may be washed with detergent or treated in various chemicals, such as aqueous ethanol, in order to remove organic residue before being mixed with growth solution. Additionally, the feather additive may be provided as a whole, in smaller pieces, or in a powder form. The feather source may be natural or synthetic. Any extracts obtained from feather may also be used as a nutrient source and are in the scope of this application. One example of such extract is a hard protein called keratin that comprises a majority of a feather's mass. The keratin may be present in the feather fiber in quantities of more than 80%, preferably more than 90% and more preferably 91% or more of the total feather mass. In other embodiments of the invention, keratin that is isolated or extracted from feather fiber may be used as a growth medium and/or nutrient source for microalgae production. Additional treatment may include compressing the feather to change its density or changing the hydrophobicity (water resistance) of the feather structure. The feather may provide carbon, nitrogen, sulfur, phosphorous, amino acids, and/or similar organic materials for algae growth as well as it may increase carbon dioxide absorption by algae. The feather fiber may also concurrently or separately serve as a physical structure for algae to grow on. Chicken feather, turkey feather, ostrich feather, duck feather, and/or feather obtained from similar domesticated avian are preferred examples of inexpensive and widely available nutrient used in the process. One type of feather fiber extract that may be used in aspects of the invention is keratin feather fiber obtained from Feather Fiber Corporation.

Algae accumulates high levels of polyunsaturated fatty acids and converts the feather fiber and/or keratinous material to accumulate unsaturated fatty acids such as the palmitic acid and/or Linolenic acid, and/or polyunsaturated acid. The unsaturated fatty acids may include omega 3, omega 6 and/or omega 9 fatty acids, any one or more of Hexadecatrienoic acid, Alpha-linolenic acid, Stearidonic acid, Eicosatrienoic acid, Eicosatetraenoic acid, Eicosapentaenoic acid, Heneicosapentaenoic acid, Docosapentaenoic acid, Docosahexaenoic acid, Tetracosapentaenoic acid, Tetracosahexaenoic acid, Linoleic acid, Gamma-linolenic acid, Eicosadienoic acid, Dihomo-gamma-linolenic acid, Arachidonic acid, Docosadienoic acid, Adrenic acid, Docosapentaenoic acid, Tetracosatetraenoic acid, Tetracosapentaenoic acid, Oleic acid, Eicosenoic acid, Mead acid, Erucic acid, Nervonic acid, α-Calendic acid, β-Calendic acid, Jacaric acid, α-Eleostearic acid, β-Eleostearic acid, Catalpic acid, Punicic acid, Rumelenic acid, α-Parinaric acid, β-Parinaric acid, Bosseopentaenoic acid, Pinolenic acid, and Podocarpic acid may be obtained from the algae grown in the method of the invention.

The temperature of the growth solution in the bioreactor is preferably in the range of 10 to 80° C., more preferably in the range of 16 to 27° C. The carbon dioxide source is preferably acquired from industrial exhausts that are expelled at high levels in which case, algae consume this as a resource, and contribute to the reduction of the adverse environmental effects or the green house effect of carbon dioxide. Such exhausts may require filtration before being provided to the algae as a growth resource. However, any source of carbon dioxide may be used for growing algae as the functionality of the process disclosed in this application is independent of the source of carbon dioxide for growing and harvesting algae.

Figure 2:
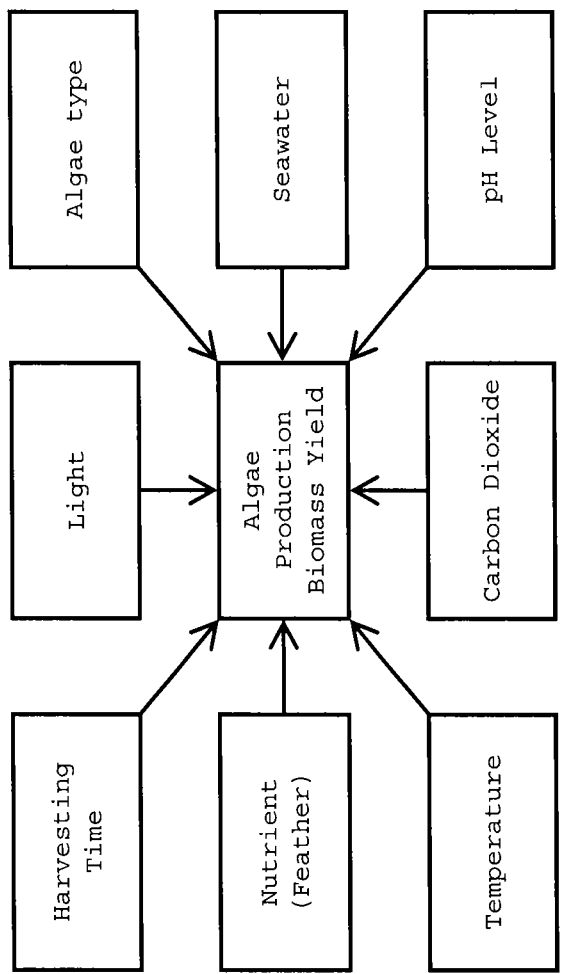
FIG. 2 illustrates the main factors that influence the occurrence, growth, cultivation, production, and biomass yield of algae.

The light source preferably includes light in wavelengths of infrared range or visible range, and more preferably, has substantial absence of UV range. The factors that influence the occurrence, growth, cultivation, and production yield of algae or biomass may be adjusted over the period of production to control and optimize the growth rate of algae. This factors are shown in FIG. 2. It is also possible to grow algae in darkness, using sugars, for example, glucose, fructose, and/or galactose, to feed the algae directly, in which case carbon dioxide is not required for growth.

Growing microalgae involves the organism's natural life process in which the algal cells increase in size and number. During the growth phase, the microalgae are circulated throughout the open-pond photo bioreactor and feather nutrient and carbon sources are added in phases during this time.

Harvesting algae is the process of gathering the algae after it has reached its optimal growth limit. The harvested algae are then separated from its growing solution and the resulting biomass is dried. The algae processing unit 16 transforms the concentrated biomass into biofuel and other useful products that is in the concentrated biomass. Examples of the processing that are preformed in the algae processing unit 16 include, but are not limited to, extraction of lipids, extraction of phosphorous, extraction of oil, dehydration, extraction proteins, extraction of carbohydrates, and recycling the concentrated biomass back to the beginning of the process.

Figure 3:
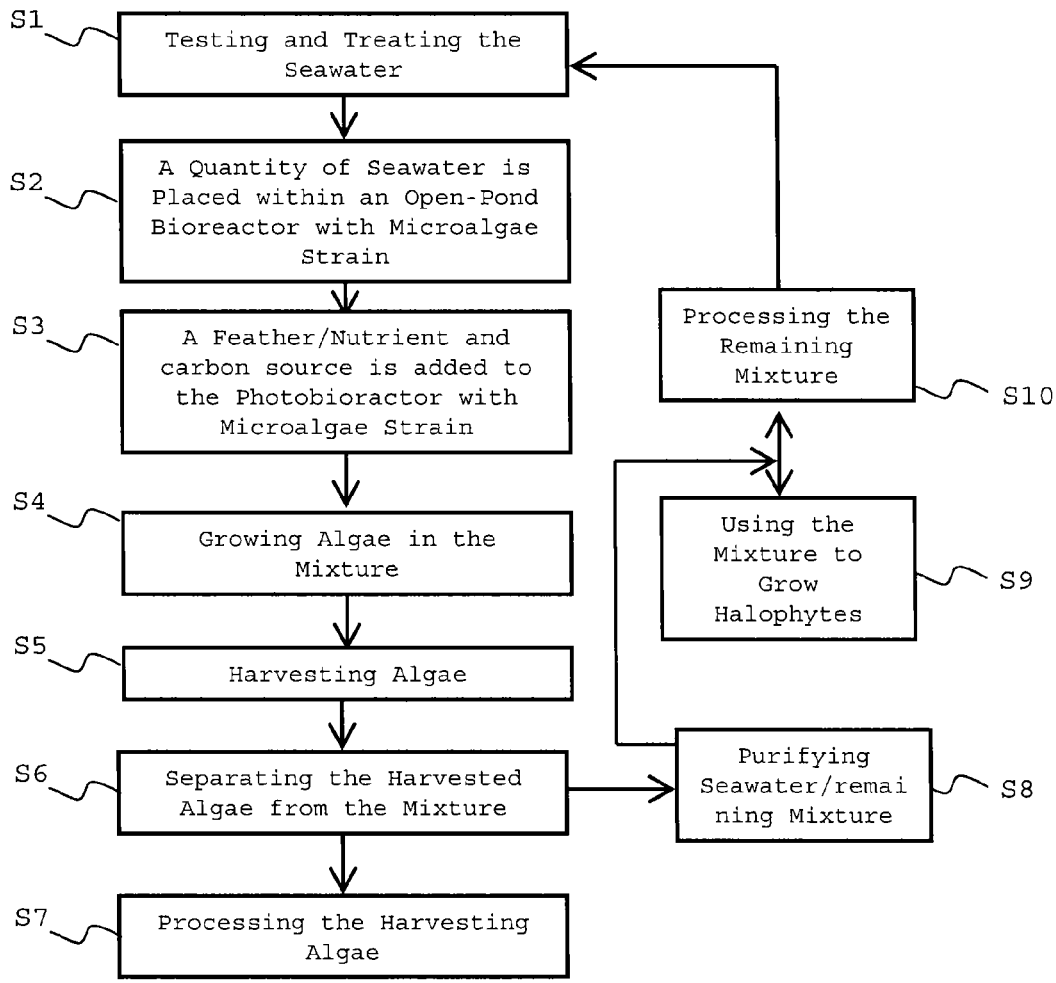
FIG. 3 is a block diagram of the process for using seawater and feather additive for harvesting algae.

The process for using seawater and feather sources for growing and harvesting algae is shown in FIG. 3. In step S1, the seawater is sequestered in an open-pond photo bioreactor where it is tested and treated in order to provide a suitable environment to circulate a strain of microalgae.

In step S2, The seawater and microalgae strain are placed within the photo bioreactor. Properties of the seawater such as temperature, pH, and/or light exposure are continually monitored and adjusted to allow a suitable environment for algae growth and reproduction.

In step S3, a feather additive and a carbon source are added to the seawater in the bioreactor. For example, in a reactor in which the algae is grown, 1%, 2%, 4%, 8%, 10%, 15%, or 20% of the reactor volume may be occupied by the feather fiber. The ratio of the weight of undissolved feather fiber to the weight of saline water may be 0.01:100 to 10:1, 0.02:100 to 5:1, 0.05:100 to 2:1, 0.1:100 to 2:1, 0.5:100 to 1:1, 1:100 to 0.5:1, 2:100 to 0.4:1, 5:100 to 0.3:1, 5:100 to 0.2:1, or 10:100 to 0.1:1, based on the total weight of the feather fiber and the total weight of the saline water.

In step S4, the microalgae reaches an adequate growth threshold and may be harvested after a period of time.

Then, in step S5, the microalgae biomass is harvested from the bioreactor in its growth solution before its separation via centrifugation.

In step S6, the algae is separated from the growth solution. Examples of methods for separation and cultivation include, but are not limited to, centrifuging, filtering, or adding and mixing chemicals that makes a suspension and enables separation of supernatant (that includes remaining salt and nutrient) from the concentrated biomass.

In step S7, the separated algal biomass is then processed into various additional byproduct such as lipids, proteins, carbohydrates, oil, vitamins, and/or similar valuable products from the concentrated biomass, dehydration, and packaging. The extracted chemicals are further processed to obtain, for example, biofuel, nutrition supplements, omega 3, nutrient for human and animal consumption, fertilizers, vitamins, chemicals, and cosmetics.

Then, the excess solution water is desalinated as indicated in step S8 and the reject water from that process is utilized for the growing halophytes as indicated in step S9. Reject water may also be devoted to processing the left over solution from the separation phase as indicated in step S10 which contributes to starting the entire cycle over again.

The invention claimed is:

1. A method for growing and/or harvesting algae, the method comprising the steps of:
   mixing seawater with feather additive in a bioreactor;
   growing the algae by digesting the feather additive with the algae;
   harvesting the algae; and
   drying a biomass formed in the harvesting step, wherein
   at least 20% by volume of the bioreactor is filled with the feather additive,
   the growing step is carried out in the bioreactor and the feather additive serves as a physical structure for the algae to grow on,
   a majority of undissolved solid materials in the mixture of the seawater and the feather additive is the feather additive, and
   the feather additive is in the form of unprocessed feathers.

2. The method according to claim 1, wherein the growing step further includes the steps of:
   adjusting a pH level of said mixture of the seawater and the feature additive;
   providing light to said mixture of the seawater and the feature additive;
   providing carbon dioxide to said mixture of the seawater and the feature additive; and
   waiting for a period of time to allow said algae to grow and further produce more of the algae in the mixture of the seawater and the feather additive.

3. The method according to claim 2, wherein the harvesting step further includes the step of:
   separating said produced more of the algae from said mixture of the seawater and the feature additive to produce the biomass and a remaining mixture.

4. The method according to claim 3, further comprising the step of:
   processing said biomass to produce biofuel.

5. The method according to claim 3, further comprising the step of:
   growing at least one strain of microalgae in the mixture of seawater and the feather additive.

6. The method according to claim 3, further comprising the step of:
   processing said biomass to produce at least one of an omega 3, a nutrient for human and animal consumption, a fertilizer, a vitamin, an oil, and/or a cosmetic byproduct.

7. The method according to claim 2, further comprising the steps of:
   adjusting said light while waiting for said period of time; and
   adjusting said carbon dioxide while waiting for said period of time.

8. The method according to claim 1, wherein said feather additive is in at least one of washed feather, clump of feather, feather extract, compact feather, chemically modified feather, or feather powder.

9. The method according to claim 1, wherein said feather additive is chicken feather, turkey feather, and/or ostrich feather.

10. The method according to claim 1, wherein said algae is of a Nannochloropsis genus.

11. The method according to claim 1, wherein a temperature of the mixture of the seawater and the feather additive in the reactor during the growing is in the range from 16° C. to 27° C.

* * * * *